United States Patent [19]

Abare

[11] Patent Number: 4,527,566
[45] Date of Patent: Jul. 9, 1985

[54] BODY WRAP
[75] Inventor: Helena E. Abare, Forsyth, Ga.
[73] Assignee: Abare Enterprises, Inc., Forsyth, Ga.
[21] Appl. No.: 464,633
[22] Filed: Mar. 14, 1983

Related U.S. Application Data

[63] Continuation of Ser. No. 205,707, Dec. 17, 1980, abandoned.

[51] Int. Cl.³ .............................................. A61F 7/00
[52] U.S. Cl. ........................................ 128/402; 128/403
[58] Field of Search ............................... 128/402-403, 128/399, 379, 384, 254, 258, 157, 327, 686

[56] References Cited

U.S. PATENT DOCUMENTS

| | | | |
|---|---|---|---|
| 1,567,931 | 12/1925 | Epler . | |
| 3,442,270 | 5/1969 | Steinman | 128/157 |
| 3,563,238 | 2/1971 | McGuire | 128/157 |
| 3,586,001 | 6/1971 | Sanderson | 128/327 |
| 3,724,457 | 4/1973 | Klatte | 128/157 X |
| 3,815,610 | 6/1974 | Winther . | |
| 3,882,867 | 5/1975 | Moran | 128/254 |
| 3,882,873 | 5/1975 | Arango | 128/402 X |
| 3,889,684 | 6/1975 | Lebold . | |
| 3,900,035 | 8/1975 | Welch et al. . | |
| 4,055,188 | 10/1977 | Pelton | 128/403 X |
| 4,081,150 | 3/1978 | Tyson | 128/402 |
| 4,092,982 | 6/1978 | Salem . | |
| 4,204,543 | 5/1980 | Henderson . | |

OTHER PUBLICATIONS

Josefek; "Omnipak" Brochure; *Health Core*, 6/1982.

Primary Examiner—Lee S. Cohen
Assistant Examiner—Angela D. Sykes
Attorney, Agent, or Firm—Jones & Askew

[57] ABSTRACT

A body wrap intended for supporting a hot or cold pack in close proximity to a localized portion of a wearer's anatomy. The wrap is relatively elongated, and has at least one open pocket to receive a hot or cold pack, such as an ice bag. The wrap is relatively inelastic in length, yet is relatively elastic in width so as to permit lateral elongation when in place around a portion of the wearer's body.

5 Claims, 5 Drawing Figures

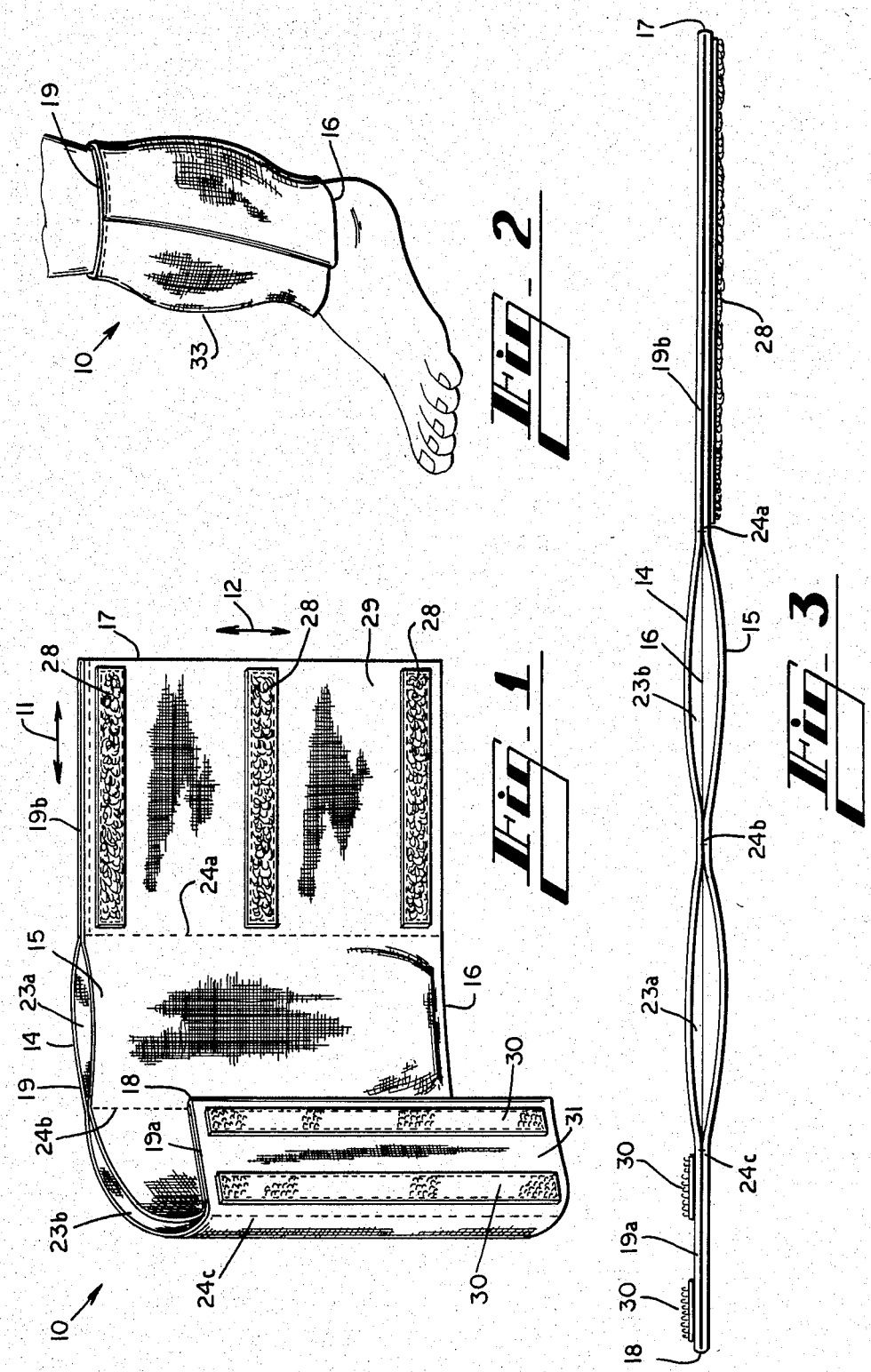

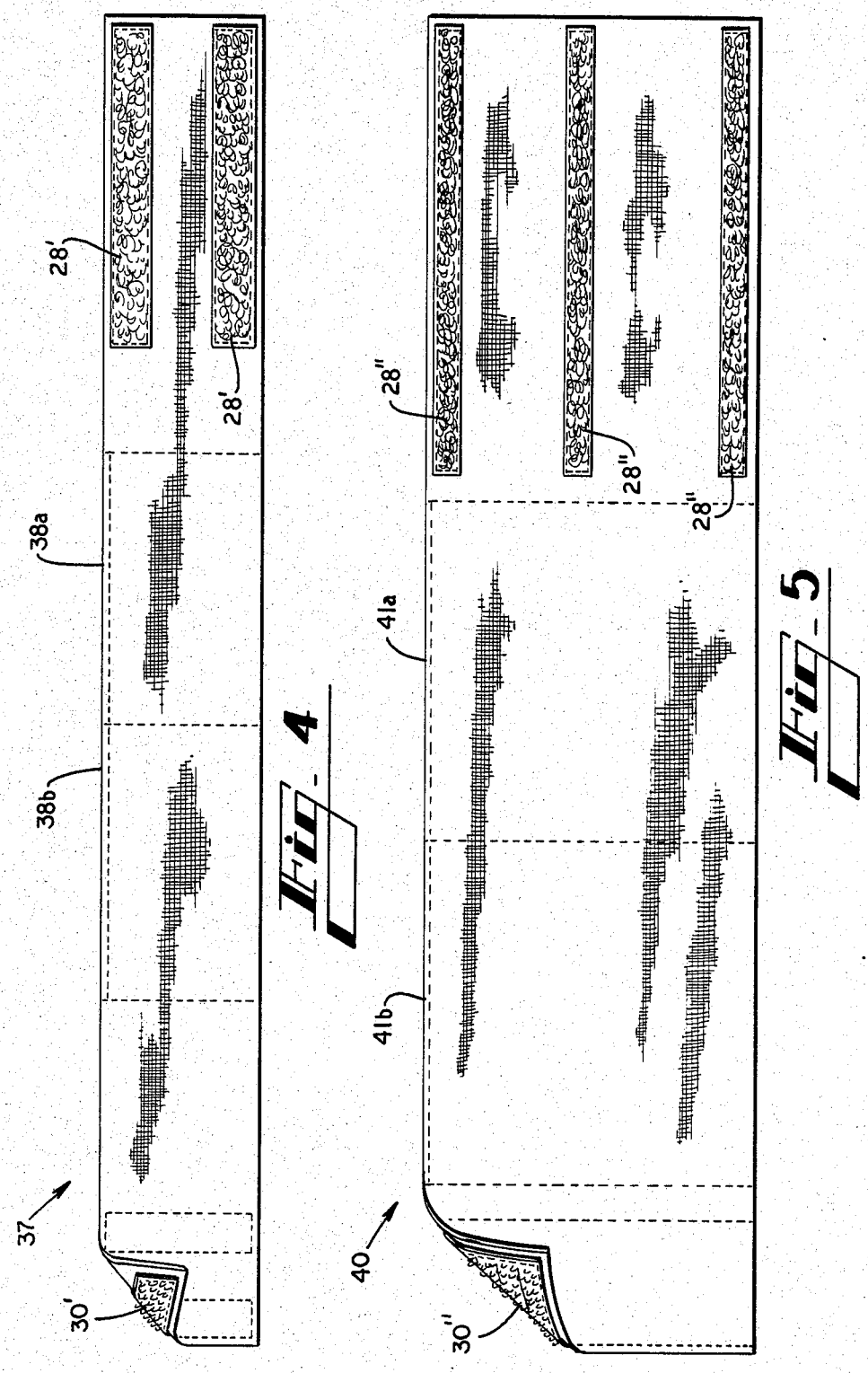

BODY WRAP

This application is a continuation of U.S. application Ser. No. 205,707, filed Dec. 17, 1980, now abandoned.

BACKGROUND OF THE INVENTION

This invention relates in general to therapeutic body wraps, and in particular relates to an improved body wrap for supporting hot or cold packs in close proximity to localized portions of the anatomy.

The application of heat or cold to various parts of the anatomy is a recognized practice for curing or alleviating various kinds of physical problems. For example, it is known to apply ice packs in an effort to reduce swelling associated with bruises or various types of surgery. It is also known to apply heat to various portions of the body in an effort to alleviate discomfort caused by muscular strain or the like.

Many devices are known for applying localized heat or cold to the anatomy. The conventional heating pad and ice bag are two examples of such prior art. While these and other similar devices meet their functional goal of heating or cooling localized portions of the body, these devices generally lack any provision for easy, quick, and secure attachment to the body portion being treated. The conventional ice bag, for example, must be manually held in place, either by the person undergoing treatment or by a nurse or aide attending the patient.

Various expedients have been proposed in an effort to maintain hot or cold packs in place on the patient's body. One commonplace expedient in hospitals and the like simply involves wrapping a towel around the affected body portion and an ice bag placed on the body, in an effort to hold in place the ice pack. For example, an ice bag is prepared and then placed against a body portion such as a patient's forehead. With the ice bag thus positioned, a towel is wrapped several times around the patient's head, with the ice bag sandwiched between the head and the innermost layer of towel. A safety pin then is attached through the free outer end of the towel and several inner layers, to prevent the towel from becoming unwound.

The foregoing technique not only is cumbersome and awkward to apply, it is also less than effective. The use of towels in this fashion is at best but a makeshift arrangement, and seldom maintains the hot or cold pack in its desired location. If the towel is wrapped tightly enough to keep the ice pack (for example) securely in place, the tightly-wrapped towel may well be uncomfortable and unpleasant to the patient. If the towel is less tightly wrapped in order to reduce patient discomfort and permit some freedom of movement, the ice pack soon slips away from its desired location on the body. Consequently, the use of towels to support hot or cold packs is at best undesirable, and can be unsatisfactory for many applications.

Various attempts have been made to provide body wraps or bands for the specific purpose of holding in place a hot or cold pack such as an ice bag or the like. These prior-art efforts typically employ various kinds of elastic bandage-like structures for holding the heat-transfer pack in place against the body, and as a result have been deficient in the ability to retain the packs in place while minimizing discomfort to the patient.

SUMMARY OF INVENTION

Accordingly, it is an object of the present invention to provide an improved body wrap.

It is another object of the present invention to provide an improved body wrap specifically intended for supporting a hot or cold pack at a desired location on the body.

It is still another object of the present invention to provide to body wrap capable of holding a hot or cold pack in place at a desired location on the body, without substantially restricting body movement.

The foregoing and other objects are accomplished according to the present invention, which includes an elongated flexible band of woven material or the like, the band having sufficient length to wrap at least once about the affected portion of the body, and having one or more pockets for receiving a hot or cold pack. The band includes fastening strips of a material permitting rapid attachment and detachment of the band ends to each other, while readily accommodating variations in size of the selected anatomical portion. Stated somewhat more specifically, the elongated flexible band of the present invention preferably is substantially nonelastic in its direction of length, yet is sufficiently elastic to permit substantial lateral elongation. The lateral resiliency of the band permits the present body wrap to be firmly held in place about the body, particularly a movable portion such as a knee or the like, while permitting lateral resiliency to accommodate body movements. At the same time, the relatively inelastic length of the band prevents the band from undergoing longitudinal elongation during body movement, so that the band tends to remain affixed in position on the body.

The nature and construction of the present invention, along with the foregoing and other objects and advantages thereof, will become more readily apparent from the following description of disclosed embodiments shown and described with respect to the drawings.

BRIEF DESCRIPTION OF DRAWINGS

FIG. 1 is a pictorial view showing a body wrap according to a first disclosed embodiment of the present invention.

FIG. 2 is a pictorial view showing the body wrap of FIG. 1 in place about the ankle of a person.

FIG. 3 is a longitudinal section view of the body wrap shown in FIGS. 1 and 2.

FIG. 4 is a plan view of an alternative embodiment of body wrap, with one corner shown turned down for illustrative purposes.

FIG. 5 is a pictorial view of still another embodiment of body wrap according to the present invention, with one corner turned down for illustrative purposes.

DESCRIPTION OF PREFERRED EMBODIMENTS

Turning first to FIGS. 1–3, there is shown generally at 10 a body wrap according to a first preferred embodiment of the present invention. The body wrap 10 in the disclosed embodiment is rectangular in overall shape, and has a longitudinal dimension denoted by the arrow 11 and a transverse or lateral dimension denoted by the arrow 12. The longitudinal dimension is herein defined as the dimension which is wrapped around a portion of a user's anatomy, such as an ankle, an elbow, or the like. It is thus conceivable, although not likely, that the dimension defined as "longitudinal" dimension 11 might actually be somewhat longer than the lateral dimension 12.

The body wrap 10 is made of two separate fabric layers or plies 14 and 15, as best seen in FIG. 3. This two-ply construction can best be obtained by starting with a single flat layer of fabric, having the desired length 11 and being approximately twice as wide as the desired width 12, and then folding the fabric laterally about an imaginary longitudinal line which bisects the fabric. The fold about this imaginary fold line thus defines the bottom edge 16 of the body wrap 10. The wrap material as thus folded is next stitched along the two ends 17 and 18, and along the portions 19a and 19b of the top edge 19. The basic rectangular configuration of the body wrap 10 is thus obtained.

A pair of pockets 23a and 23b are formed in the body wrap 10. These pockets are open along the upper edge 19 of the body wrap, and the pocket walls are defined by the individual plies 14 and 15 which make up the body wrap. The sides of the pockets 23a and 23b are conveniently defined by lateral rows of stitching 24a, 24b, and 24c extending across the body wrap 10. As best seen in FIG. 3, the sides of pocket 23b are defined by spaced-apart rows of stitching 24a and 24b, and the pocket 23a is similarly formed by the spaced-apart rows of stitching 24b, 24c. The bottom of each pocket is closed, and is formed by the unitary bottom edge 16 of the body wrap 10 in the disclosed embodiment. The unstitched portions of the upper edge 19, between stitched portions 19a and 19b, provide the openings of the pockets 23a and 23b.

The structure of the body wrap 10 is completed by adding the fastening means which allow the wrap to be adjustably secured in place about a desired portion of the user's anatomy. On the body wrap 10 these fastening means are provided by at least one strip 28 of fastening material affixed to one side 29 of the body wrap 10 adjacent the end 17, and by at least one other strip 30 of complementary fastening material attached to the other side 31 of the body wrap adjacent the end 18. The complementary fastening strips 28 and 30 are advantageously provided by a hook-and-loop material such as Velcro material or the like. The strips 28 are three in number, in the embodiment of FIG. 1, and are spaced equidistant across the width of the body wrap in longitudinal alignment with the wrap. Two strips of fastening material 30 are provided, both being laterally disposed across the width of the body wrap, in closely spaced-apart relation adjacent the end 18 of the body wrap. The individual strips 28 and 30 of fastening material are attached to the body wrap by any suitable technique, such as conventional stitching or the like.

It should be apparent that the number of individual strips of fastening material used at the ends of the body wrap, and particularly the number of longitudinally-aligned strips 28 disposed in lateral spaced-apart relation adjacent end 17 of the body wrap, depends on the physical dimensions of the body wrap and of the strips of fastening material. The use of three strips 28 in FIG. 1 is by way of example only, and is not considered to be a limiting factor.

The body wrap 10 is preferably fabricated from a woven material whose exterior surface is relatively soft and comfortable in contact with a person's body. The material also should be sufficiently lightweight and porous to allow the material to "breathe" while wrapped around the body, so as to minimize sweating due to entrapment of perspiration. Whatever the choice of material, it is important that the body wrap 10 be relatively nonelastic in the longitudinal direction 11, so that the selected overall length of the body wrap remains substantially unchanged as the body wrap undergoes tension. The fabric of the body wrap should be relatively elastic in the lateral dimension 12, however, allowing the body wrap to undergo a substantial amount of lateral resilient elongation. The reason for lateral elongation will become apparent below.

The longitudinally-disposed strips 28 of fastening material may themselves be relatively inelastic, but the narrowness and longitudinal placement of those strips do not materially affect the desired overall lateral elasticity of the body wrap 10. The laterally-extending fastening strips 30 at the end 18 of the body wrap do inhibit the lateral elasticity of the wrap at that end, for a purpose described below.

FIG. 2 illustrates a typical application of the body wrap 10, in place about an ankle of an individual. Assuming it is desired to reduce swelling in a sprained ankle by locally applying cold packs to the ankle, one or two suitable cold packs first are prepared. These cold packs (not shown) may be provided simply by filling suitable waterproof containers, such as conventional thin bags made of thin plastic film such as polyethylene or the like, with a quantity of crushed ice. Polyethylene bags of this kind are commonly available, and collect the water remaining as the ice melts. While the choice of a particular bag, or indeed the use of a bag, is not critical, it may be desirable to use bags equipped with a watertight zipper-type closure. The ice-containing bags are inserted in the individual pockets 23a and 23b, through the open ends at the top edge 19, and the wrap 10 is suitably positioned about the person's ankle. While one end of the wrap (for example) end 18, is manually held in place against the ankle, the body wrap 10 is snugly wrapped around the ankle so that the longitudinal strips 28 of fastening material at the other end 17 overlap the laterally-disposed strips 30 of fastening material at the one end. The overlapping strips of fastening material mutually adhere, thereby preventing the body wrap 10 from becoming unwrapped from the person's ankle.

The lateral elasticity of the body wrap 10 accommodates the physical bulk of the ice packs as the wrap is positioned around the patient's ankle. The body wrap may thus bulge outwardly as shown at 33 in FIG. 2, because the inner surface of the rap is snugly disposed against the ankle. As the ice melts, the lateral elasticity of the body wrap tends to draw inwardly the relatively elongated area 33 surrounding the ice packs, so as to maintain the ice-retaining pockets 23a and 23b in snug contact with confronting areas of the patient's body.

The lateral elasticity of the body wrap 10 also allows the in-place wrap to expand and contract, as the patient's ankle flexes during normal movement of the body. Thus, a person wearing the wrap 10 around his or her ankle as shown in FIG. 2, is not impeded by the wrap from walking or otherwise moving the ankle. At the same time, the relative inelasticity of the body wrap prevents longitudinal elongation of the wrap as the ankle moves, and thereby tends to maintain the wrap snugly engaged around the periphery of the ankle. The inelastic bands 30 of fastening material extending laterally of the wrap adjacent its end 18 prevent lateral elongation of the wrap adjacent its interconnected ends, and thereby assist in retaining the wrap in place around the wearer's ankle or other movable portion of the body.

Although the foregoing discussion assumes the body wrap 10 is used with a cold pack such as ice bags, it should be apparent that any alternative source of heat or cold may be substituted in the pockets 23a and 23b of the body wrap. Moreover, the individual pockets themselves may be provided with a water-resistant lining if desired, although providing a water-impervious lining as part of the wrap increases its cost and may reduce the desired lateral elasticity of the wrap.

FIG. 4 shows another disclosed embodiment 37 of body wrap according to the present invention. The wrap 37 differs from the previously-described wrap 10 primarily in overall length, and in its length-width ratio. The body wrap 37 is specifically intended to support ice packs or the like adjacent the eyes of a wearer, and so the wrap 37 is long enough to wrap around the entire head of the wearer. The wrap 37 is considerably narrower than the previously-described wrap 10, which was intended for use on a wearer's ankle or elbow. Because of its relative narrowness, the wrap 10 has but two longitudinally-extending strips 28' of fastening material.

The body wrap 37 may be fabricated in the same manner as described above, and similarly has a pair of pockets 38a and 38b open to receive and retain ice packs or the like. In use, the pockets of the body wrap 37 first are filled with suitable ice packs or the like. The wrap is then placed around the patient's head in suitable orientation to place the ice-containing pockets 38a and 38b in desired exposure to the affected portion of the head. For example, the body wrap may be positioned to place the pockets in surrounding relation to one eye of the wearer. The fastening strips 28' and 29' at the ends of the wrap are then mutually engaged, to maintain the wrap in place. As described previously, the ice packs placed in the pockets 38a and 38b may advantageously contained in waterproof bags forming no part of the present invention, so as to contain the water as the ice melts.

FIG. 5 shows yet another embodiment 40 of the present invention, and it should be noted that this Figure is drawn to a different scale from that of the body wrap 37 depicted immediately above in FIG. 4. The body wrap 40 is intended to fit around the entire upper torso of a person, and has sufficient width to cover a substantial portion of the torso. For example, a torso wrap 40 according to the present invention may be approximately twelve inches wide (unelongated) and approximately forty-eight inches long, so as to encompass a relatively wide range of torso sizes. The longitudinal bands 28" should be long enough to permit securing the wrap 40 to the smallest anticipated torso size. In the torso wrap having dimensions described above, each of the bands 28" is approximately sixteen inches long, and four separate lateral fastening bands 30" are provided at the opposite end of the wrap, thereby providing an effective torso size range somewhat greater than sixteen inches.

The overall size of the torso wrap 40 enables that wrap to be used for applying either heat or cold to relatively large body portions such as the back or chest. The size or number of pockets in the torso wrap 40, or in any body wrap according to the present invention, are considered to be matters of choice, depending primarily on the particular application for which the wrap is intended. In that regard, it should now be understood that wraps of various lengths and widths can be readily prepared for fitting specific body portions such as the jaw, the knee, the shin, the shoulder, and others in addition to the body members described above. Furthermore, the present invention is adaptable for wraps intended to cover smaller portions of the body, such as an individual hand or foot.

It should also be understood that the foregoing relates only to specific embodiments of the present invention, and that numerous changes and modifications may be made therein without departing from the spirit and scope of the invention as defined in the following claims.

I claim:

1. A flexible wrap for enveloping a selected portion of the human anatomy and supporting a thermal pack in heat transfer relation to the anatomical portion, the wrap comprising:
    an elongated flexible band of material having sufficient overall length to wrap around a selected anatomical portion, and having substantial overall width less than said length;
    said band being substantially flat;
    securement means connected to said band to detachably interconnect the ends of said band when wrapped around the selected anatomical portion, said securement means being operative to secure said band in snug wrapped engagement at any selected length between certain minimum and maximum circumferences of body portion encirclement;
    said band being relatively inelastic in length, so as to remain in position snugly wrapped around said anatomical portion irrespective of body movement tending to cause lengthwise elongation of the band;
    said band being relatively elastic in width so as to permit substantial lateral elongation of the band in response to distention of said anatomical portion during movement;
    inelastic means extending across the width of said band adjacent an end thereof and operatively associated with the band to inhibit the widthwise elasticity of the band at said end, thereby rendering said end of the band relatively inelastic in width as well as in length so as to assist in retaining the wrap in place around the anatomical portion; and
    at least one compartment formed in said band to removably receive a quantity of thermal material, so that the thermal material in said compartment is in heat transfer relation with the anatomical portion about which said band is wrapped;
    so that the lengthwise inelasticity of the band prevents elongation of the band and thereby maintains the band in place wrapped around an anatomical portion despite possible anatomical movement accommodated by the lateral elasticity of the band, and so that the inelasticity in both width and length at the end of the band prevents widthwise elongation at the end and thereby assists in retaining the flexible wrap in place on the anatomical portion.

2. A wrap as in claim 1, wherein said securement means comprises:
    at least one first strip of hook and loop fastener material disposed on one side of said band, and extending longitudinally a distance inwardly from one end of said band; and
    at least one second strip of mating fastener material disposed on the other side of said band, adjacent the other end of said band and extending laterally of the band, so that said first and second strips of fastener material are disposed in mutually confronting relation for mating engagement when said band is snugly wrapped around said anatomical portion, whereby the band remains so wrapped until the strips of mating fastener material are unfastened.

3. A wrap as in claim 2, wherein:

said band comprises two flat interconnected layers of material each overlying the other to provide a unitary said band;

said two layers being mutually unattached for a distance along one longitudinal edge of said band, thereby permitting an access opening to the region between said two layers; and means laterally disposed across said band on both sides of said access opening to laterally interconnect said layers, thereby defining said compartment in said band for receiving a quantity of thermal material, said compartment having sides that are elastically deformable to accommodate the thermal material because of said elasticity in width of said band.

4. A wrap as in claim 2, wherein:

said laterally disposed second strip of fastening material is relatively inelastic and defines said inelastic means, and is secured to said band so that the inelasticity of the second strip prevents the width of said band from elastically elongating at said other end;

thereby preventing said fastener strips from lateral elongation when mutually interconnected, and thus keeping said band snugly wrapped despite possible movement of said anatomical portion.

5. A wrap as in claim 1, wherein:

said band comprises two layers of material folded laterally to define one longitudinal edge of the band;

at least two separate lateral interconnecting means extending along the width of said folded layers and interconnecting said folded layers;

said lateral interconnecting means being spaced apart along the longitudinal extent of said band so that said compartment is formed between said two layers making up said band, said folded longitudinal edge defining the bottom of said compartment and the top of said compartment being open between the edges of said folded layers to receive said thermal material; and both of said folded layers being relatively inelastic in length and being relatively elastic in width so as to resiliently accommodate the physical bulk of the thermal material as well as possible body movement without undergoing substantial longitudinal elastic elongation.

* * * * *